(12) United States Patent
Boaz

(10) Patent No.: US 6,362,343 B1
(45) Date of Patent: Mar. 26, 2002

(54) PROCESS FOR HALOHYDRIN PREPARATION

(75) Inventor: Neil W. Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/693,687

(22) Filed: Oct. 23, 2000

Related U.S. Application Data

(62) Division of application No. 09/290,205, filed on Apr. 9, 1999, now Pat. No. 6,162,924.

(51) Int. Cl.$^7$ ............... C07D 233/84; C07D 301/27
(52) U.S. Cl. ................... 548/317.5; 549/514
(58) Field of Search ............ 548/317.5; 549/514

(56) References Cited

U.S. PATENT DOCUMENTS

| | | |
|---|---|---|
| 4,020,250 A | 4/1977 | Lal |
| 4,434,071 A | 2/1984 | Powell |
| 5,147,893 A | 9/1992 | Mueller et al. |
| 5,248,817 A | 9/1993 | Auerbach et al. |
| 5,420,343 A | 5/1995 | Koszyk et al. |
| 5,476,944 A | 12/1995 | Partis et al. |
| 5,602,418 A | 2/1997 | Lin et al. |

FOREIGN PATENT DOCUMENTS

| | | |
|---|---|---|
| EP | 02-28285 A2 * | 3/1987 |
| EP | 238285 | 9/1987 |
| EP | 617036 A2 | 9/1994 |
| EP | 658550 A2 | 6/1995 |
| WO | WO 93/10087 | 5/1993 |
| WO | WO 96/28402 | 9/1996 |

OTHER PUBLICATIONS

Coe et al., *J. Chem. Soc.* Perkin I, (1991) 2373–2377.
Baker and Wiemer, *J. Org. Chem*, (1998) 2613–2618.
H1475, Newman et al. Aug. 1, 1995.
Morrison and Boyd, Organic Chemistry, Jan. 1975, 3$^{rd}$ Edition, pgs 180 and section 6.14.
Wang et al., Can Bioorg. Med. Chem. Lett. 1998, 7,2567 (Abstract).

* cited by examiner

*Primary Examiner*—Alan L. Rotman
*Assistant Examiner*—Rita Desai
(74) *Attorney, Agent, or Firm*—Michael J. Blake; Bernard J. Graves, Jr.

(57) ABSTRACT

A process for preparing a halohydrin of a water-miscible olefin comprising: reacting a water-miscible olefin in water with a compound of the formula (I)

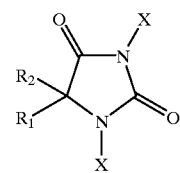

(I)

wherein $R_1$ and $R_2$ independently represent a branched or unbranched, substituted or unsubstituted, lower alkyl having from 1 to 5 carbons and X is a halogen, to thereby form the halohydrin of the water-miscible olefin.

16 Claims, No Drawings

PROCESS FOR HALOHYDRIN PREPARATION

This application is a divisional of, and claims the benefit of, application Ser. No. 09/290,205, filed on Apr. 9, 1999, now U.S. Pat. No. 6,162,924 which status is allowed, which application is hereby incorporated herein by reference.

FIELD OF THE INVENTION

This invention relates to preparing a halohydrin of a water-miscible olefin.

BACKGROUND OF THE INVENTION

Substituted tetrahydrofuran molecules are becoming of greater importance in pharmaceutical and agrochemical applications. 3,4-Epoxytetrahydrofuran (EpTHF) is an important building block for many of these substituted tetrahydrofurans. For example, EpTHF has been used to prepare anti-HCMVP agents (Wang, et al. *Can. Biorg. Med. Chem. Lett.* 1997, 7, 2567) and antibacterial agents (Kirkup and Boland, *Eur. Pat. Appl.* EP 238285, 1987). The preparation of EpTHF has been reported through standard oxidation techniques using peracids, but these reactions are rather slow and product isolation is difficult. In addition, there are safety concerns about contacting a peracid species with a known peroxide former such as 2,5-dihydrofuran.

An alternative method for the preparation of epoxides involves the initial formation of a halohydrin of the olefin followed by ring-closure under basic conditions. This method avoids the use of a strong oxidant but does require an efficient halohydrin formation. The halohydrin of the olefin is normally formed by the reaction of the corresponding hypohalous acid (normally formed in situ) with the olefin.

Sources of the hypohalous acid include a mixture of the halogen (bromine or chlorine) with water, acidification of the hypohalite anion (especially sodium or calcium hypochlorite), or N-haloacetaimide or N-halosuccinimide in water. Indeed, 3-bromo-4-hydroxytetrahydrofuran has been prepared by the action of aqueous N-bromosuccinimide on 2,5-dihydrofuran (Kirkup and Boland, *Eur. Pat. Appl.* EP 238285, 1987; Baker and Wiemer, *J. Org. Chem.* 1998, 63, 2613). However, the selectivity of these halide sources when forming halohydrins is poor because of competing reactions.

Halohydrin forming reactions all suffer from the presence of two divergent pathways: the formation of halohydrin and the formation of dihalide. For example, as illustrated by the reaction scheme A outlined below, upon reaction with 2,5-dihydrofuran (2,5-DHF), two reaction products are formed.

Reaction Scheme A

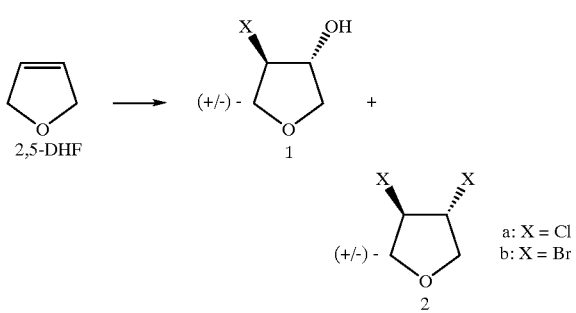

In reaction scheme A, the desired halohydrin 1 and the undesired dihalide 2 are formed from the 2,5-dihydrofuran. This is particularly the case when using bromine in water, in which the dibromide 2b is the major product. The use of freshly recrystallized N-bromosuccinimide as the bromine source does not afford clean conversion to 1b, because even in this case 14% of the undesired dibromide 2b is formed. Moreover, the use of dilute sodium hypochlorite (acidified with hydrochloric acid) affords significant amounts (15–25%) of the dichloride 2a.

The brominating agent 1,3-dibromo-5,5-dimethylhydantoin has also been used for bromohydrin preparation (Coe et al., *J. Chem. Soc. Perkin I*, 1, 1991, 2373). However, 1,3-dibromo-5,5-dimethylhydantoin has not been used to form bromohydrins of water-miscible olefins. Moreover, 1,3-dibromo-5,5-dimethylhydantoin has previously been used mainly as an oxidant, for allylic bromination of olefins, or for aromatic brominations. The allylic bromination and aromatic bromination reactions are substitution reactions that often proceed via a free radical mechanism. In contrast, in accordance with the discoveries of the present invention, bromohydrin formation from an olefin using 1,3-dibromo-5,5-dimethylhydantoin is an electrophilic addition reaction that adds two species to the olefin and generally proceeds via an ionic mechanism. There is no precedent that suggests superior selectivity for bromohydrin formation when using 1,3-dibromo-5,5-dimethylhydantoin as compared to other electrophilic bromine sources.

Therefore, a process that improves the selective conversion of a water-miscible olefin to halohydrin is still needed. The present invention solves this problem by providing such an improved process.

SUMMARY OF THE INVENTION

In accordance with the purpose(s) of this invention, as embodied and broadly described herein, this invention, in one aspect, relates to a process for preparing a halohydrin of a water-miscible olefin comprising reacting a water-miscible olefin in water with a compound of the formula (1)

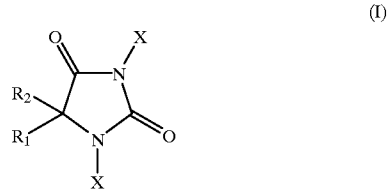

(I)

wherein $R_1$ and $R_2$ independently represent a branched or unbranched, substituted or unsubstituted, lower alkyl having from 1 to 5 carbons and X is a halogen, to thereby form the halohydrin of the water-miscible olefin.

In another aspect, the present invention relates to a process for preparing trans-3-bromo-4-hydroxytetrahydrofuran from 2,5-dilydrofuran comprising reacting 2,5-dihydrofuran in water with a compound of the formula (I)

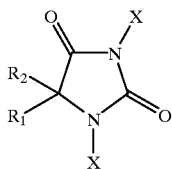

wherein $R_1$ and $R_2$ are both methyl groups and X is Br, to thereby form trans-3-bromo-4-hydroxytetrahydrofuran.

In yet another aspect, the present invention relates to a process for the preparation of an epoxide of a water-miscible olefin comprising the steps of (a) reacting a water-miscible olefin in water with a compound of the formula (I)

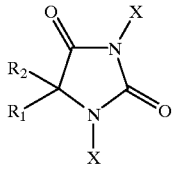

wherein $R_1$ and $R_2$ independently represent a branched or unbranched, substituted or unsubstituted, lower alkyl having from 1 to 5 carbons and X is a halogen, to thereby form a halohydrin of the water-miscible olefin; and (b) treating the resulting halohydrin with base to form an epoxide of the water-miscible olefin.

In yet another aspect, the present invention relates to a process for the in situ preparation of 3,4-epoxytetrahydrofuran comprising the steps of: (a) reacting 2,5-dihydrofuran with 1,3-dibromo-5,5-dimethylhydantoin in water to form trans-3-bromo-4-hydroxytetrahydrofuran, and (b) treating the resulting trans-3-bromo-4-hydroxytetrahydrofuran with base to form 3,4-epoxytetrahydrofuran.

Additional advantages of the invention will be set forth in part in the detailed description which follows, and in part will be obvious from from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention and the Examples included therein.

Before the present processes, compounds and/or compositions are disclosed and described in detail, it is to be understood that this invention is not limited to these specific synthetic processes and conditions, for specific processes or process conditions for preparing a halohydrin from from a water-miscible olefin as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an olefin" includes mixtures of olefin compounds, and the like.

Ranges may be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

In this specification and in the claims which follow, reference will be made to a number of terms which shall be defined to have the following meanings.

The term "water-miscible" as used herein with respect to olefin refers to the ability of a liquid olefin to dissolve uniformly in liquid water. Preferably, the olefin is completely miscible in water. However, lesser degrees of miscibility will still work in the invention herein, although it is understood that the more miscible, the more preferable. The term "solubility" is often used synonymously with miscibility in reference to liquids, but it more properly applies to solids. When applied to liquids, the olefin is preferably fully soluble in water.

The term "selective conversion" or "selectivity" as used herein refers to the formation of the halohydrin product from a water miscible olefin and a compound of formula (I). The halohydrin formation is expressed in terms of a mole percent of halohydrin formed relative to the mole percent formation of the other undesired product, a dihalide.

A "weight percent" of a component, unless specifically stated to the contrary, is based on the total weight of the formulation or composition in which the component is included.

In one embodiment, the present invention is directed to a process for preparing a halohydrin of a water-miscible olefin comprising reacting a water-miscible olefill in water with a compound of the formula (I)

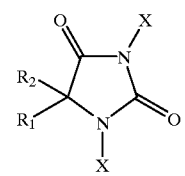

wherein $R_1$ and $R_2$ independently represent a branched or unbranched, substituted or unsubstituted, lower alkyl having from 1 to 5 carbons and X is a halogen, to thereby form the halo hydrin of the water-miscible olefin.

The water-miscible olefini used in the process of this invention can be mono to tetra substituted, cyclic or acyclic. Preferably, the water-miscible olefin is a heteroatom-containing olefini with less than or equal to 6 carbon atoms and the heteroatom is oxygen, sulfur or nitrogen. Preferred water-miscible olefins include dihydrofurans (2,3-dihydrofuran and 2,5-dihydrofuran), 2,3-dihydropyran, 2,5-dihydrothiophene-1,1-dioxide, and epoxybutene. The most preferred water-miscible olefin is 2,5-dihydrofuran.

The water-miscible olefin used in the process of this invention is miscible in water. Preferably, the water-miscible olefin is miscible at concentrations of at least 0.1 weight percent olefin in water.

The $R_1$ and $R_2$ substituents of the compound of formula (I) are independent and are preferably lower alkyl groups.

The term "lower alkyl" as used herein refers to a branched or unbranched, substituted or unsubstituted, hydrocarbon group of 1 to 5 carbon atoms, such as methyl, ethyl, n-propyl, isopropyl, n-butyl, isobutyl, t-butyl, n-pentyl, isopentyl, neopentyl, t-pentyl and the like. In addition, the lower alkyl groups may be substituted with ethers and their derivatives, thioethers and their derivatives and halogens among others. Preferred lower alkyl groups herein contain 1 to 2 carbons. Most preferably, $R_1$ and $R_2$ are both methyl groups.

In formula (I), the X substituent is a halogen. X is Br, Cl, I or F, more preferably X is Br. Most preferably, the process of this invention uses the compound of the formula (I) wherein $R_1$ and $R_2$ are both methyl groups and X is Br.

Although the process conditions may vary, the amount of water used in the process is such that the starting concentration of the water-miscible olefin is preferably from 1 to 4 molar. However, this concentration may be lower to accommodate olefin-water miscibility constraints. Further, the reaction temperature is preferably from 5° C. to 25° C. According to this process, the selective conversion to halohydrin is typically greater than or equal to 90%.

In another embodiment, the present invention is directed to a process for preparing trans-3-bromo-4-hydroxytetrahydrofuran from 2,5-dihydrofuran comprising reacting 2,5-dihydrofuran in water with a compound of the formula (I)

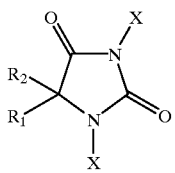

(I)

wherein $R_1$ and $R_2$ are both methyl groups and X is Br, to thereby form trans-3-bromo-4-hydroxytetrahydrofuran. The amount of water is such that the starting concentration of 2,5-dihydrofuran is preferably from 1 to 4 molar. The reaction temperature is preferably from 5° C. to 25° C. The selective conversion to trans-3-bromo-4-hydroxytetrahydrofuran is typically greater than 98%.

In another embodiment, the present invention is directed to a process for the preparation of an epoxide of a water-miscible olefin comprising the steps of: (a) reacting a water-miscible olefin in water with a compound of the formula (I)

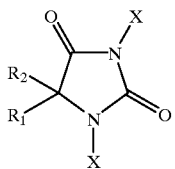

(I)

wherein $R_1$ and $R_2$ independently represent a branched or unbranched, substituted or unsubstituted, lower alkyl having from 1 to 5 carbons and X is a halogren, to thereby form a halohydrin of the water-miscible olefin; and (b) treating the resulting halohydrin with base to form an epoxide of the water-miscible olefin. The epoxide from this process is preferably prepared in situ, that is, step (b) is performed in the same reaction vessel as step (a).

Preferred embodiments for $R_1$, $R_2$, X, and the water-miscible olefin, and process conditions are as defined above under the halohydrin of a water-miscible olefin section. In a preferred form of the epoxide preparation process of this invention, the water-miscible olefin is 2,5-dihydrofuran and the amount of water is such that the starting concentration of 2,5-dihydrofuran is from 1 to 4 molar. Preferably, $R_1$ and $R_2$ are both methyl groups and X is Br. The step (a) reaction temperature is preferably from 5° C. to 25° C. In a preferred embodiment, the resulting halohydrin is trans-3-bromo-4-hydroxytetrahydrofuran and the epoxide is 3,4-epoxytetrahydrofuran.

Step (b) of the epoxide preparation process involves treating the resulting halohydrin with base to form an epoxide of the water-miscible olefin. Step (b) is a well known organic epoxide synthesis wherein the treatment of a halohydrin with a base is an intramolecular ether synthesis (intramolecular substitution). That is, the nucleophilic oxygen atom and electrophilic carbon atom are in the same molecule. Preferably, the base used in step (b) is an alkali or alkaline earth hydroxide or carbonate, and more preferably, the base is sodium hydroxide.

In yet another embodiment, the present invention is directed to a process for the in situ preparation of 3,4-epoxytetrahydrofuran comprising (a) reacting 2,5-dihydrofuran with 1,3-dibromo-5,5-dimethylhydantoin in water to form trans-3-bromo-4-hydroxytetrahydrofuran, and (b) treating the resulting trans-3-bromo-4-hydroxytetrahydrofuran with base to form 3,4-epoxytetrahydrofuran. The base is preferably sodium hydroxide. The amount of water is such that the starting concentration of 2,5-dihydrofuran is preferably from 1 to 4 molar. The step (a) reaction temperature is preferably from 5° C. to 25° C.

The starting compounds of the invention may be readily synthesized using techniques generally known to synthetic organic chemists. Suitable experimental methods for making and derivatizing compounds are described, for example, in the references cited in the Background section herein above, the disclosures of which are hereby incorporated by reference for their general teachings and for their synthesis teachings. Methods for making specific and preferred compounds of the present invention are described in detail in Examples 1, 2 and 3 below.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.); however, some errors and deviations may have occurred. Unless indicated otherwise, parts are parts by weight, temperature is in ° C. or is at ambient temperature, and pressure is at or near atmospheric.

The term "amount" of a compound or property as provided herein means that such amount as is capable of performing the function of the compound or property for which an amount is expressed. As will be pointed out below, the exact amount required will vary from process to process, depending on recognized variables such as the compounds employed and the processing conditions observed. However, an appropriate amount may be determined by one of ordinary skill in the art using only routine experimentation.

Example 1

Preparation and Isolation of trans-3-bromo-4-hydroxytetrahydrofuran 1,3-dibromo-5,5-dimethylhydantoin (143 g; 0.50 mol; 1.0 equiv) was slurried in water (500 mL) and cooled in ice-water. 2,5-dihydrofuran (76 mL; 1.0 mol) was added slowly dropwise over 1 hour such that the temperature of the reaction mixture remained below 20° C. After the addition was complete the reaction mixture was allowed to warm to room temperature and stir for 5 hours. GC analysis (area percent) indicated a ratio of trans-3-bromo-4-hydoxytetrahydrofuran (1b) to 3,4-dibromotetrahydrofuran (2b) of 98.5:1.5. The reaction mixture was extracted three times with ethyl acetate (with sodium chloride addition to facilitate layer separation), and the combined organic solution was dried with magnesium sulfate and concentrated to afford 198.8 g of crude product which contained substantial amounts of 5,5-dimethylhydantoin. This material was treated with a 1:1 mixture of ethyl acetate:heptane, filtered, and concentrated. This was repeated to afford 159.71 g of crude bromohydrin (1b). This material was 86% pure ($^1$H NMR analysis), to indicate a yield of 82%.

trans-3-bromo-4-hydroxytetrahydrofuran (1b): $^1$H NMR (CDCl$_3$) δ4.58–4.52 (m, 1H); 4.399 (dd, 1H, J=4.40, 10.71 Hz); 4.240 (dd, 1H, J=4.40, 6.87 Hz); 4.21–4.17 (m, 1H); 4.066 (dd, 1H, J=1.92, 10.44 Hz); 3.799 (dd, 1H, J=1.37, 9.89 Hz); 3.35 (br s, 1H). GC (30 m DB-17, 50° C., 10 min, 50–200° C., 15°/min, 100° C., 5 min): t$_R$ 14.43 min.

3,4-dibromotetrahydrofuran (2b): $^1$H NMR (CDCl$_3$) δ4.7–4.58 (m, 4H); 4.24 (d, 2H, J=10.3 Hz). GC (30 m DB-17, 50° C., 10 min, 50–200° C., 15°/min, 100° C., 5 min): t$_r$ 14.28 min.

The trans-3-bromo-4-hydroxytetrahydrofuran compound prepared in Example 1 is an intermediate in the preparation of 3,4-epoxytetrahydrofuran, which is a useful building block for a variety of substituted tetrahydrofurans. Substituted tetrahydrofuran molecules are finding increased usefulness in the pharmaceutical and agrochemical industries.

It was quite surprising to observe that the use of 1,3-dibromo-5,5-dimethylhydantoin as the bromonium ion source in water afforded highly selective conversion of 2,5-dihydrofuran to bromohydrin, with the selectivity routinely greater than 98%. Further, the 1,3-dibromo-5,5-dimethylhydantoin reacts very smoothly with 2,5-dihydrofuran to form the bromohydrin. This bromohydrin can be isolated or can be used in situ to form the desired 3,4-epoxytetrahydrofuran in high yield by treatment with base, preferably sodium hydroxide, as described below in Example 3.

Example 2

Preparation of trans-3-chloro-4-hydroxytetrahydrofuran 1,3-dichloro-5,5-dimethylhydantoin was used in a process as outlined in Example 1. Although the conversion was 29% based on 0.5 molar equivalent of reagent (1.0 equivalent of Cl), the selectivity ratio of chlorohydrin (1a) to dichloride (2a) was 93.6: 6.4 using 1,3-dichloro-5,5-dimethylhydantoin.

Example 3

Preparation of 3,4-epoxytetrahydrofuran (EpTHF)

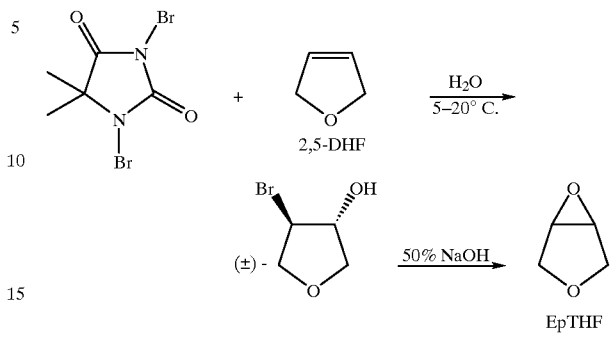

1,3-Dibromo-5,5-dimethylhydantoin (143 g; 0.50 mol; 1.0 equiv) was slurried in water (500 mL) in a 1-L 3-necked flask equipped with an overhead stirrer and an addition funnel. The mixture was cooled in an ice-water bath and at 6° C. the slow addition dropwise of 2,5-dihydrofuran (76 mL; 1.0 mol) was begun. The addition was carried out over 50 min such that the temperature remailed below 20° C. After the addition was complete, the reaction mixture was stirred in the cold water bath for 30 min. The bath was allowed to warm over 1 hour to 20° C. or approximately room temperature. The reaction mixture was stirred for a further 2.5 hours at this temperature. The reaction mixture was sampled and GC analysis (area percent) showed a large conversion to trans-3-bromo-4-hydroxytetrahydrofuran and indicated a minimal amount of residual 2,5-dihydrofuran (2,5-DHF). A ratio of trans-3-bromo-4-hydroxytetrahydrofuran to undesired 3,4-dibromotetrahydrofuran of 98.2:1.8 was observed in the GC analysis. Further stirring at ambient temperature afforded no further conversion according to GC analysis. The reaction mixture was placed in a cool water bath (about 15° C.) and 50% sodium hydroxide (88 g; 1.1 mol; 1.1 equiv) was added and washed with a small amount of water. This resulted in an immediate exotherm (maximum reaction mixture temperature 35° C.) with the reaction mixture first turning cloudy then clear and pale yellow. The mixture was allowed to return to ambient temperature over 30 min at which point GC analysis indicated a complete consumption of trans-3-bromo-4-hydroxytetrahydrofuran with formation of 3,4-epoxytetrahydrofuran. The reaction mixture was transferred to a separatory funnel and extracted with five 100-mL portions of dichloromethane (DCM). The combined extracts were dried with sodium sulfate and the solvent was removed at reduced pressure. The crude product was distilled at reduced pressure with minimal fractionation to afford 49.5 g (58%) of 3,4-epoxytetrahydrofuran, bp 62° C./35 mm Hg, which was >99% pure by GC analysis.

Analysis of the remaining aqueous layer by quantitative internal standard GC indicated that 32.6 g (38%) of 3,4-epoxytetrahydrofuran remained in the aqueous solution.

$^1$H NMR (CDCl$_3$) δ4.007 (d, 2H, J=10.44 Hz); 3.777 (s, 2H); 3.636 (d, 2H, J=10.16 Hz). GC (30 m DB-17, 50° C., 10 min, 50–200° C., 15°/min, 100° C., 5 min): t$_R$ 9.39

Comparative Example 1

Reaction of 2,5-dihydrofuran with N-bromosuccinimide in Water

Freshly recrystallized N-bromosuccinimide (8.9 g; 50 mmol; 1.0 equiv) was slurried in water (18.75 mL). The mixture was cooled in cool water and 2,5-dihydrofuran (3.8 mL; 50 mmol) was added dropwise over 15 min with no apparent exotherm. The reaction mixture was allowed to warm to room temperature and stir for 5 hours to consume most of the 2,5-dihydrofuran (GC analysis). Analysis of the reaction mixture indicated the presence of both trans-3-bromo-4-hydroxytetrahydrofuran (1b) and 3,4-dibromotetrahydrofuran (2b) in a ratio of 86:14 (area percent GC). This result was identical to that using reagent-grade N-bromosuccinimide.

Comparative Example 2

Reaction of 2,5-dihydrofuran with Bromine in Water

Bromine (1.29 mL; 25 mmol; 1.0 equiv) was added to 12.5 mL of water to afford a reddish yellow mixture. The mixture was cooled in ice water and 2,5-dihydrofuran (1.89 mL; 25 mmol) was added dropwise. By the end of the addition the reddish yellow color had disappeared. The mixture was stirred for 30 min at which point GC analysis indicated almost no 2,5-dihydrofuran. However, the major product observed was 3,4-dibromotetrahydrofuran (2b), which was present in a 78:22 ratio with trans-3-bromo-4-hydroxytetrahydrofuran (1b) according to GC analysis (area percent).

Comparative Example 3

Reaction of 2.5-dihydrofuran with Sodium hypochlorite/hydrochloride Acid

A 5.25% aqueous solution of sodium hypochlorite (35.4 g; 25 mol; 1.0 equiv) was combined with 2,5-dihydrofuran (1.89 mL; 25 mmol). The mixture was cooled to −5° C. A 3 M solution of hydrochloric acid (8.3 mL; 25 mmol; 1.0 equiv) was added slowly dropwise such that the temperature remained between −5 and −10° C. The reaction mixture was stirred at −5 to −10° C. for 30 min, at which point GC analysis indicated 55% conversion and a selectivity ratio of trans-3-chloro-4-hydroxytetrahydrofuran (1a) to 3,4-dichlorotetrahydrofuran (2a) of 79:21. A portion of the reaction mixture was extracted three times with ethyl acetate, and the combined extracts were dried with magnesium sulfate and concentrated. $^1$H NMR analysis of the mixture indicated that (1a) was the major product.

trans-3-chloro-4-hydroxytetrahydrofuran (1a): $^1$H NMR (CDCl$_3$) δ4.5–4.44 (m, 1H); 4.302 (dd, 1H, J=4.67, 10.16 Hz); 4.23–4.14 (m, 2H); 3.960 (dd, 1H, J=1.65, 10.16 Hz); 3.82–3.76 (m, 1H); 2.2 (br s, 1H). GC (30 m DB-17, 50° C., 10 min, 50–200° C. 15°/min, 100° C., 5 min): $t_R$ 13.15 min.

3,4-dichlorotetrahydrofuran (2a): $^1$H NMR (CDCl$_3$) δ4.5–4.4 (m, 4 H); 4.2–4.0 (m, 2 H). GC (30 m DB-17, 50° C., 10 min, 50–200° C., 15°/min, 100° C., 5 min): $t_R$ 11.28 min.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein.

It is intended that the specification and examples be considered as exemplary only, with a true scope and spirit of the invention being indicated by the following claims.

What is claimed is:

1. A process for the preparation of an epoxide of a water-miscible olefin of a dihydrofuran, dihydropyran, dihydrothiophene, or an epoxybutene, the process comprising the steps of:
   (a) reacting the water-miscible olefin in water with a compound of the formula (I)

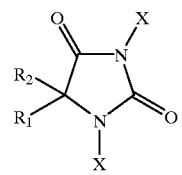

wherein R$_1$ and R$_2$ independently represent a branched or unbranched, substituted or unsubstituted, lower alkyl having from 1 to 5 carbons and X is a halogen, to thereby form a halohydrin of the water-miscible olefin; and
   (b) treating the resulting halohydrin with base to form an epoxide of the water-miscible olefin.

2. The process of claim 1, wherein the water-miscible olefin is 2,5-dihydrofuran.

3. The process of claim 1, wherein R$_1$ and R$_2$ are both methyl groups and X is Br.

4. The process of claim 1, wherein the halohydrin is trans-3-bromo-4-hydroxytetrahydrofuran.

5. The process of claim 1, wherein the epoxide is 3,4-epoxytetrahydrofuran.

6. The process of claim 1, wherein the base is an alkali or alkaline earth hydroxide or carbonate.

7. The process of claim 1, wherein the base is sodium hydroxide.

8. The process of claim 1, wherein the epoxide is prepared in situ.

9. The process of claim 1, wherein the amount of water is such that the starting concentration of water-miscible olefin is from 1 to 4 molar.

10. The process of claim 1, wherein the step (a) reaction temperature is from 5° C. to 25° C.

11. The process of claim 1, wherein the water-miscible olefin is 2,3-dihydrofuran.

12. The process of claim 1, wherein the water-miscible olefin is 2,3-dihydropyran, 2,5-dihydrothiophene-1,1-dioxide or epoxybutene.

13. A process for the in situ preparation of 3,4-epoxytetrahydrofuran comprising the steps of:
   (a) reacting 2,5-dihydrofuran with 1,3-dibromo-5,5-dimethylhydantoin in water to form trans-3-bromo-4-hydroxytetrahydrofuran, and (b) treating the resulting trans-3-bromo-4-hydroxytetrahydrofuran with base to form 3,4-epoxytetrahydrofuran.

14. The process of claim 13, wherein the base is sodium hydroxide.

15. The process of claim 13, wherein the amount of water is such that the starting concentration of 2,5-dihydrofuran is from 1 to 4 molar.

16. The process of claim 13, wherein the step (a) reaction temperature is from 5° C. to 25° C.

* * * * *